(12) United States Patent
Hsu Huang et al.

(10) Patent No.: US 11,890,130 B2
(45) Date of Patent: Feb. 6, 2024

(54) PICKUP DIAPHRAGM

(71) Applicant: JAZZ HIPSTER CORPORATION, New Taipei (TW)

(72) Inventors: Yueh-Hua Hsu Huang, New Taipei (TW); Lien-Huang Yang, New Taipei (TW); Ching-Hui Huang, New Taipei (TW)

(73) Assignee: JAZZ HIPSTER CORPORATION, New Taipei (TW)

( * ) Notice: Subject to any disclaimer, the term of this patent is extended or adjusted under 35 U.S.C. 154(b) by 0 days.

(21) Appl. No.: 17/830,131

(22) Filed: Jun. 1, 2022

(65) Prior Publication Data

US 2023/0389887 A1    Dec. 7, 2023

(51) Int. Cl.
*A61B 7/02* (2006.01)
*G10K 13/00* (2006.01)

(52) U.S. Cl.
CPC .............. *A61B 7/02* (2013.01); *G10K 13/00* (2013.01)

(58) Field of Classification Search
CPC ........................................ A61B 7/02
USPC ........................................ 181/131
See application file for complete search history.

(56) References Cited

U.S. PATENT DOCUMENTS

| | | | | |
|---|---|---|---|---|
| 3,020,971 A * | 2/1962 | Cefaly | ............... | A61B 7/02 181/137 |
| 4,440,258 A * | 4/1984 | Packard | ............... | A61B 7/02 181/137 |
| 5,945,640 A * | 8/1999 | Rossini | ............... | A61B 7/026 181/131 |
| 6,244,376 B1 * | 6/2001 | Granzotto | ............... | A61B 7/02 181/131 |
| 9,801,606 B2 * | 10/2017 | Shan | ............... | A61B 7/04 |
| 10,213,181 B2 * | 2/2019 | Keller | ............... | A61B 7/02 |
| 10,398,406 B2 * | 9/2019 | Keller | ............... | A61B 7/02 |
| 2006/0018487 A1 * | 1/2006 | Smith | ............... | H04R 31/003 381/423 |
| 2018/0344282 A1 * | 12/2018 | Lin | ............... | A61B 7/02 |
| 2020/0098345 A1 * | 3/2020 | Loriaux | ............... | A61B 7/02 |
| 2021/0038183 A1 * | 2/2021 | Ting | ............... | G10K 13/00 |
| 2022/0323042 A1 * | 10/2022 | Wong | ............... | A61B 7/02 |

FOREIGN PATENT DOCUMENTS

WO    WO-2020072561 A1 *   4/2020   ............... A61B 7/00

* cited by examiner

*Primary Examiner* — Jeremy A Luks
(74) *Attorney, Agent, or Firm* — Muncy, Geissler, Olds & Lowe, P.C.

(57) ABSTRACT

A pickup diaphragm includes a pickup part, a suspension edge and an outer edge, wherein the pickup part includes a non-planar surface. The suspension edge includes a deformable surface, with a joint surface being respectively configured on the inner and outer sides of the deformable surface, and the joint surface on the inner side being fixedly connected to the periphery of the non-planar surface. In addition, the outer edge includes a ring groove, in which one side of the ring groove is set as a connection end while the other side thereof is set as an opening end, the inner side of the connection end is fixedly connected to the joint surface located on the outer side, and a stethoscope head can be inserted through the opening end such that the ring groove is placed in sleeve on the outside of the stethoscope head.

5 Claims, 11 Drawing Sheets

PICKUP DIAPHRAGM

BACKGROUND OF THE INVENTION

1. Field of the Invention

The present invention relates to a pick diaphragm which can be applied as an audio receiving component placed in sleeve on a stethoscope head.

2. Description of Related Art

It is well known that, in prior art, the pickup device can be applied to receive the physiological sound of the human body, and it is called a stethoscope when used in medical usages. Among them, there are comparatively old-fashioned wired stethoscopes as well as wireless electronic stethoscopes. It should be appreciated that, no matter wired stethoscopes or wireless electronic stethoscopes, most of them are internally equipped with a contact-typed microphone and, when the stethoscope is in contact with the human body, the target sound can be collected/picked up.

In the prior art stethoscope, the sound pickup component in contact with the human body is installed in sleeve with a planar diaphragm, and the plane of the planar diaphragm in contact with the human body can merely provide the audio reception feature during the sound collection/pickup process. However, the audio generated by the human body may include many other subtle vibrations, and the planar diaphragm cannot fully receive them effectively due to its low sensitivity.

SUMMARY OF THE INVENTION

The pickup diaphragm of the present invention configures a design combining at least two different materials and shapes, using the relative linkage relationship between such different materials and shapes in order to make the movement between such two parts show high flexibility thereby improving the sensitivity for the vibration reception of subtle audio during the audio pickup process. So, this is the solution for the pickup diaphragm provided by the present invention.

The present invention discloses a pickup diaphragm which is detachably installed in sleeve on a stethoscope head, comprising a pickup part for receiving the audio, a suspension edge for enhancing the vibration sensitivity as well as an outer edge for the combination onto the stethoscope head, wherein the pickup part includes a non-planar surface which is concave toward the stethoscope head; the suspension edge includes a deformable surface, in which a joint surface is respectively configured on the inner and outer sides of the deformable surface, and the joint surface on the inner side is fixedly connected to the periphery of the non-planar surface; and the outer edge includes a ring groove, in which one side of the ring groove is set as a connection end while the other side thereof is set as an opening end, the inner side of the connection end is fixedly connected to the joint surface located on the outer side, and the stethoscope head is inserted through the opening end, such that the ring groove is placed in sleeve on the outside of the stethoscope head.

Thereby that, the deformable surface has a relative linkage relationship with the non-planar surface, and since the deformable surface is located around the non-planar surface, it is possible to provide good elasticity upon performing audio pickup operations, thus enhancing the flexibility during movement between them two.

In a preferred embodiment, the pickup part and the suspension edge are configured to have different materials and shapes.

In a preferred embodiment, the pickup part is manufactured by means of bio-compatible PP (Polypropylene) materials.

In a preferred embodiment, the suspension edge is manufactured by means of fabrics processed with bio-compatible surface treatment.

In a preferred embodiment, the outer edge is manufactured by means of elastic PP materials.

In a preferred embodiment, the non-planar surface is an arc-shaped or tapered surface.

In a preferred embodiment, the deformable surface is an arc-shaped or arbitrary curved surface.

DETAILED DESCRIPTION OF THE PREFERRED EMBODIMENTS

Other technical contents, aspects and effects concerning the present invention can be clearly appreciated through the detailed descriptions on the preferred embodiments of the present invention in conjunction with the appended drawings.

As used in the present Specification, the terms "inner" and "internal" describing a structural position refer to a position close to the center of the structural body, or a position that is non-exposed in use; the term "inward" refers to a position toward the center of the structural body, or toward a non-exposed position in use; the terms "outer", "external", "periphery" or "surrounding" refer to the position away from the center of the structural body, or an exposed position in use; and the term "outward" refers to a position away from the center of the structural body, or toward an exposed position in use.

In addition, as used in the present Specification, the term "on" for describing a structure position refers to any surface position of the structure, rather than the commonly known terms "above" or "upper" implicitly including directional characteristics. On the other hand, the terms "above" and "below" used to describe a structural position refer to the directionality of the structural position under conventional usage.

Besides, as used herein, the terms "fixedly installed", "installed in sleeve" or "fixedly installed in sleeve" for describing the structural combination relationship generally refer to the fact that multiple structures will not be easily separated or dropped off after being combined, which may be a fixed connection or a detachable connection, an integrally formed connection, a mechanical connection, an electrical connection, or a direct physical connection, or else an indirect connection by means of an intermediate medium; for example, by using any one approach of the threads, tenons, fasteners, nails, adhesives, high-frequency waves or pressure combination, and the "installed in sleeve" or "fixedly installed in sleeve" means that one structure is externally combined with another structure.

Figure 1:
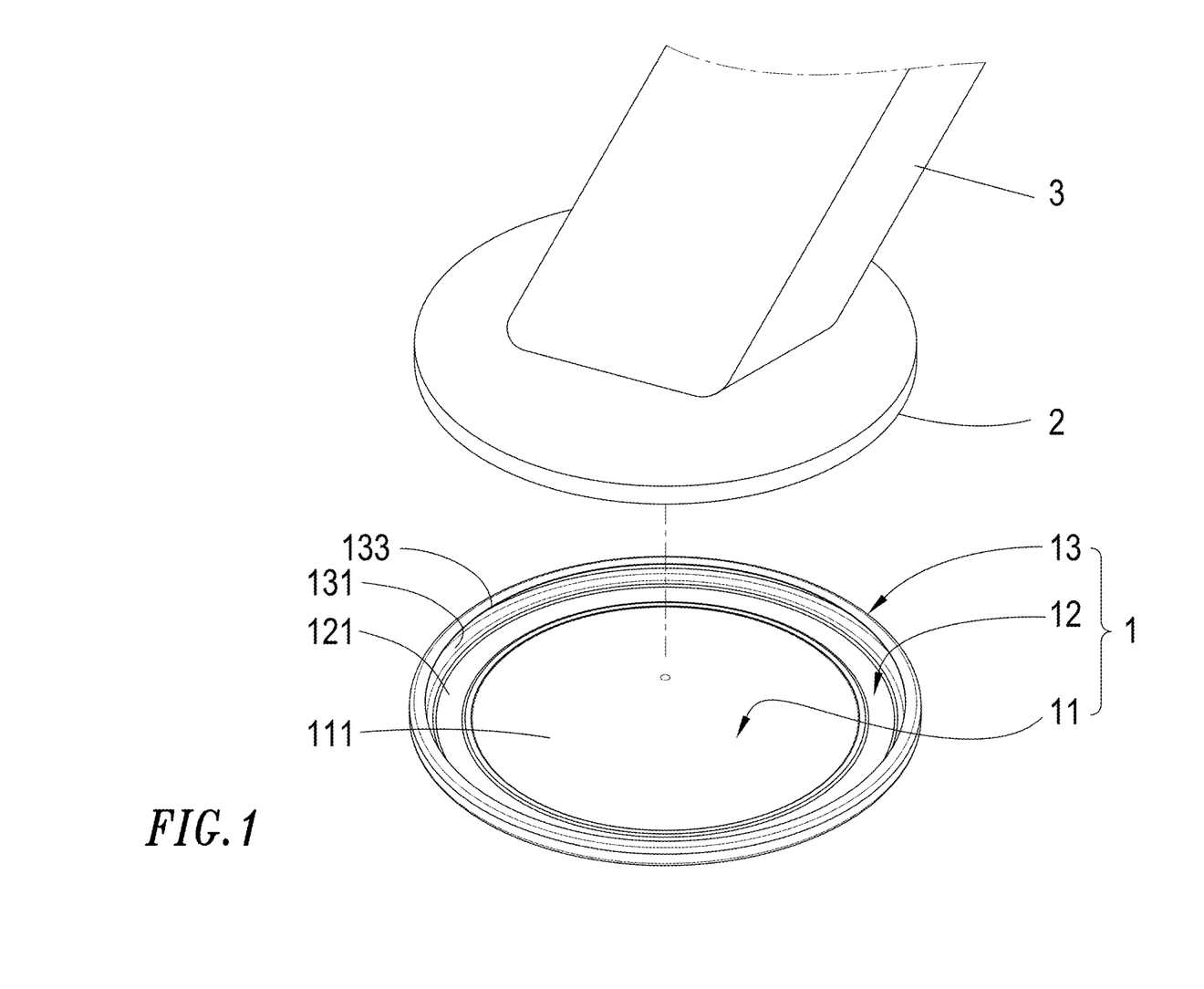
FIG. 1 shows a stereo disassembled view for the combination of the stethoscope with the pickup diaphragm according to the present invention.
Figure 2:
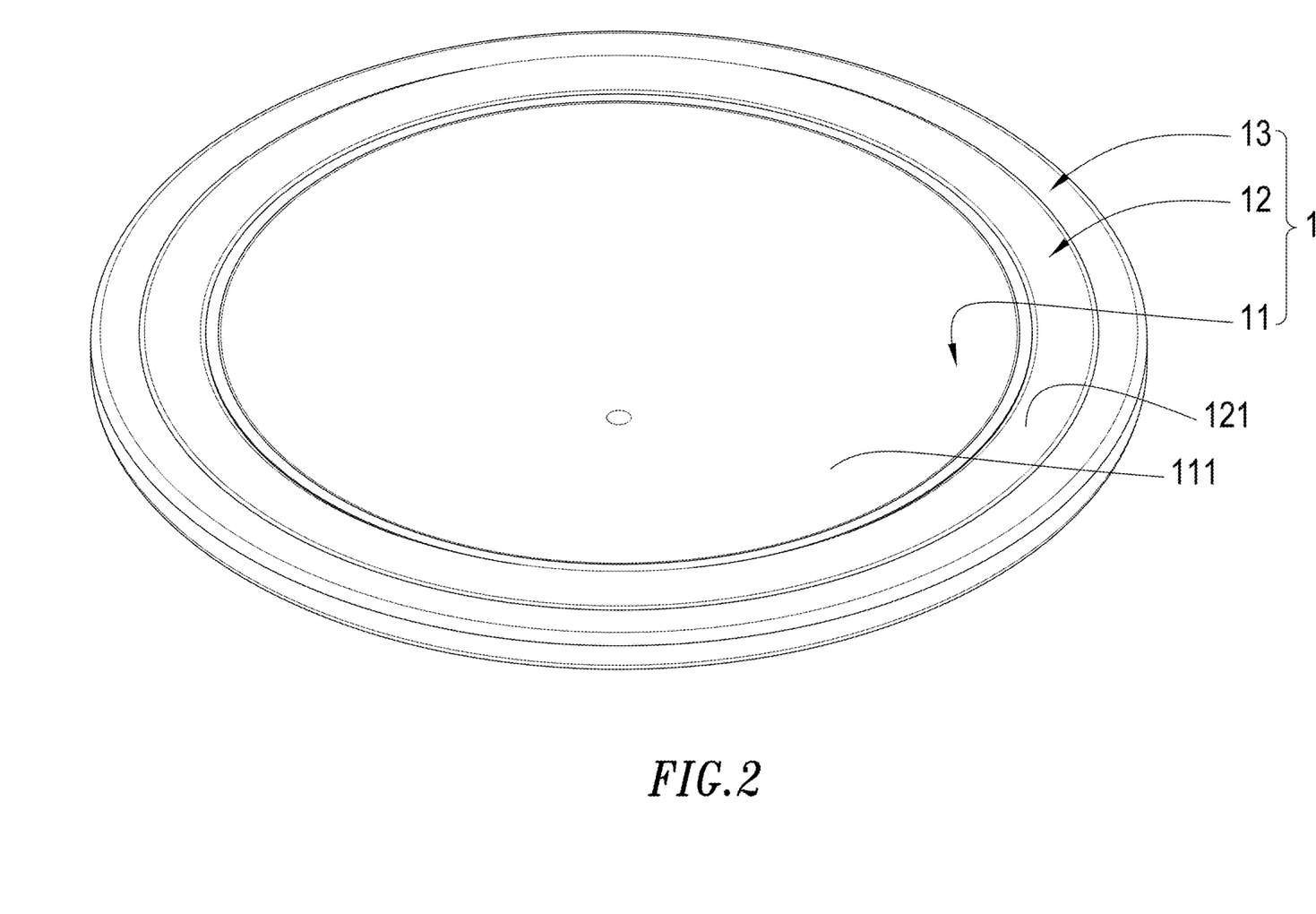
FIG. 2 shows a stereo view of the pickup diaphragm according to the present invention.

Now, referring to FIGS. 1 and 2, it can be seen that the pickup diaphragm 1 according to the present invention is used to be fixedly installed in sleeve on the stethoscope head 2 of a stethoscope, in which the pickup diaphragm 1 includes a pickup part 11 for audio receptions, a suspension edge 12 for enhancing vibration sensitivity, and an outer edge 13 used to be jointed onto the stethoscope head 2.

Figure 3:
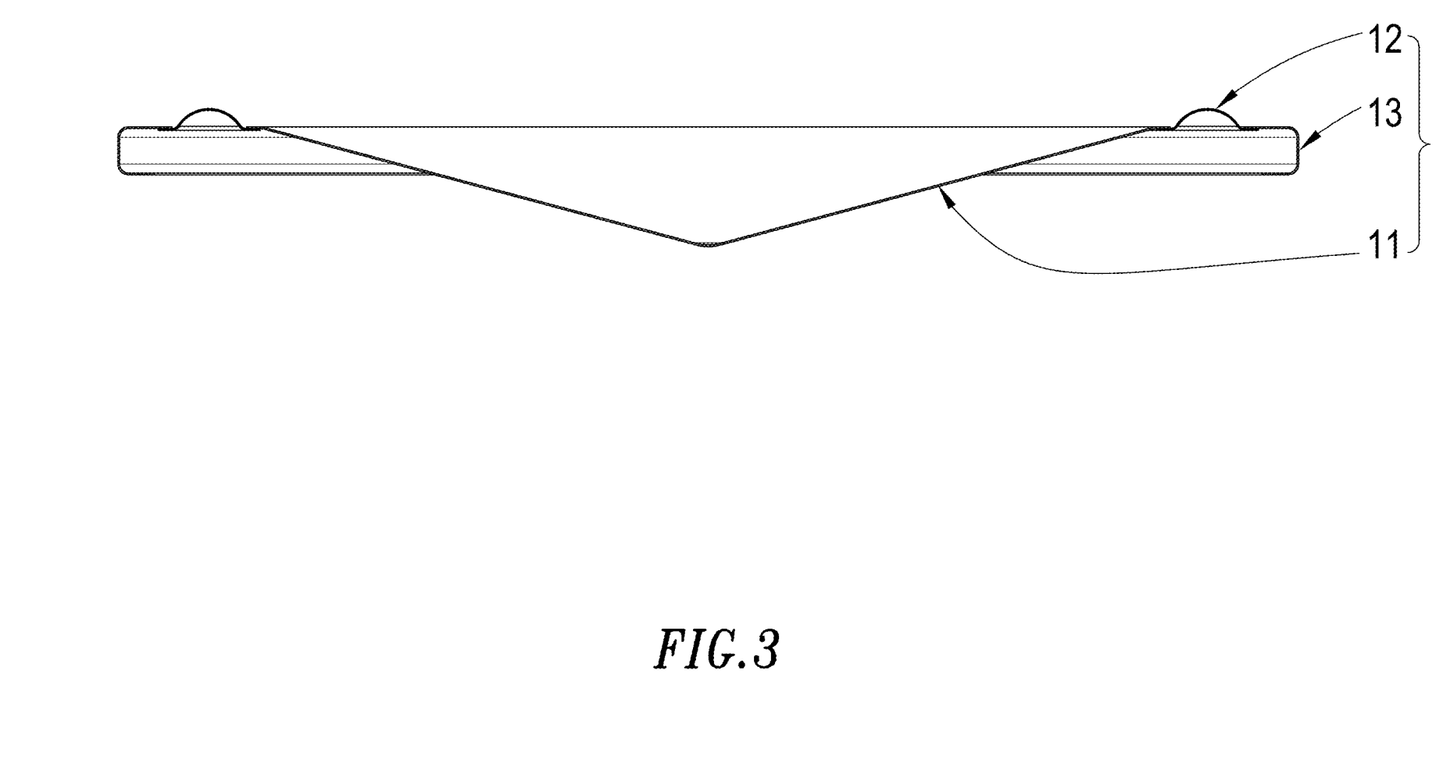
FIG. 3 shows a cross-section view of the pickup diaphragm according to the present invention.
Figure 4:
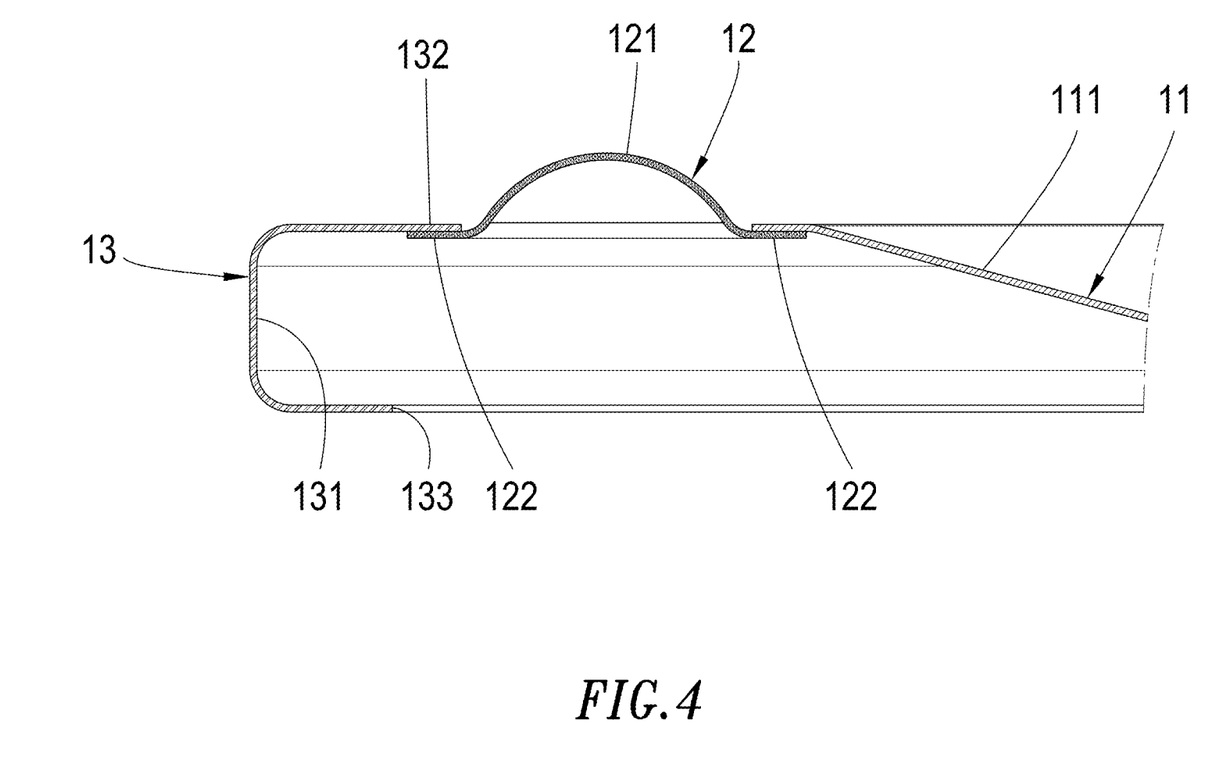
FIG. 4 shows a partial cross-section view of the pickup diaphragm according to the present invention.

Herein, referring to FIGS. 2-4, the pickup part 11 includes a non-planar surface 111 which is concave toward the stethoscope head 2 and may be an arc-shaped or tapered surface; the suspension edge 12 is fixedly connected to the surrounding of the pickup part 11 and has a deformable surface 121 which may be an arc-shaped surface or an arbitrary curved surface, and a joint surface 122 is respectively configured on the inner and outer sides of the deformable surface 121, and the joint surface 122 on the inner side is fixedly connected to the periphery of the non-planar surface 111.

Next, referring to FIGS. 2-5, the pickup part 11 is manufactured by means of bio-compatible PP (Polypropylene) materials, the suspension edge 12 is manufactured by means of fabrics processed with bio-compatible surface treatment (e.g., coating), the pickup part 11 and the suspension edge 12 are configured to have different materials and shapes, and the deformable surface 121 has a relative linkage relationship with the non-planar surface 111, so that, upon performing audio pickup processes, the suspension edge 12 is in contact with the patient's skin surface 4, and the deformable surface 121 is located around the non-planar surface 111 in order to provide good elasticity when picking up sound, thereby that the flexibility between such two parts can be improved, and the reception for the vibrations of subtle audios during the pickup process can be more sensitive; at the same time, the non-planar surface 111 can adjust different frequency responses by using the above-mentioned curved surface or tapered surface, so as to improve the overall sound pickup effect.

Moreover, referring to FIGS. 1-4, herein the outer edge 13 includes a ring groove 131, and one side of the ring groove 131 is set as a connection end 132, while the other one thereof is set as an opening end 133. The inner side of the connection end 132 is fixedly connected to the outer side of the joint surface 122, so the stethoscope head 2 can be inserted through the opening end 133 such that the ring groove 131 can be placed in sleeve onto the outside of the stethoscope head 2.

Also, the outer edge 13 is made of PP material with better elasticity, which can provide a more stable wrapping property so as to facilitate the placement in sleeve onto the outside of the stethoscope head 2.

Figure 5:
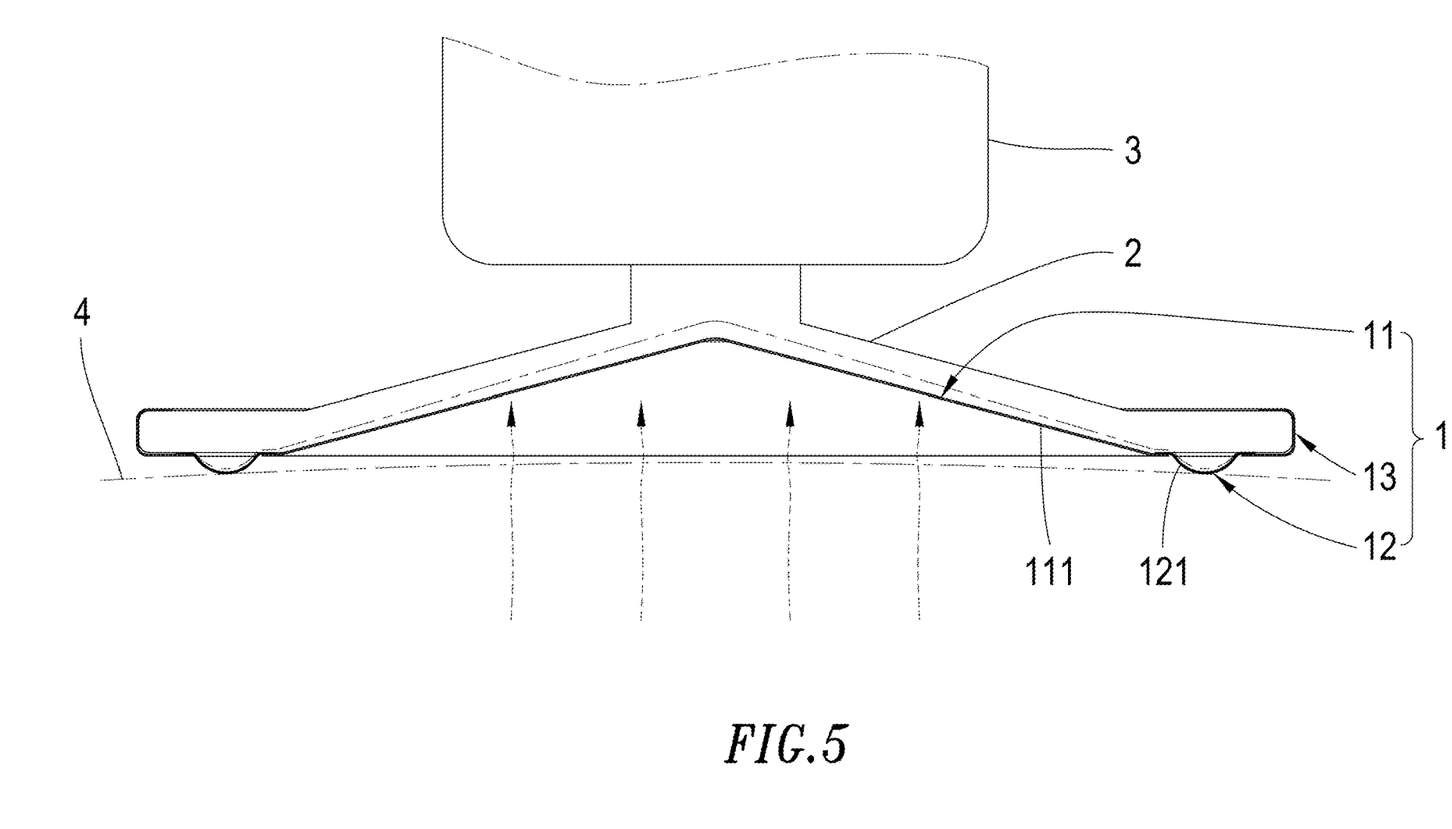
FIG. 5 shows a view for the audio pickup practice of the pickup diaphragm according to the present invention.

In addition, referring to FIGS. 1 and 5, the stethoscope head 2 in the present invention is connected to a host 3, and both the stethoscope head 2 and the host 3 can use existing auscultation instruments currently available on the market.

Comparing the pick diaphragm 1 according to the present invention with the conventional planar diaphragm products by means of the following approaches, the test contents and results are illustrated and explained in details as below:

Test Item 1—Comparative Tests of the Present Invention and Conventional Products Under Idle Noise The test hardware is configured in an anechoic chamber, and the test objects are stethoscopes/heads using the pickup diaphragm according to the present invention and stethoscopes/heads using conventional planar diaphragm products. Besides, the stethoscope/head of the pickup diaphragm according to the present invention is tested in three specifications: Bell mode, Diaphragm mode, and Extended Range mode, which is sequentially and respectively placed on the speaker (closed state) inside the test environment in a diaphragm surface facing-up fashion, then transmitting the sound to the computer where the ACQUAlyzer has been installed by way of the Bluetooth transmitter in order to observe the sound reception condition of the test object at the receivable maximum sound reception level (gain: 0 dB).

Figure 6A:
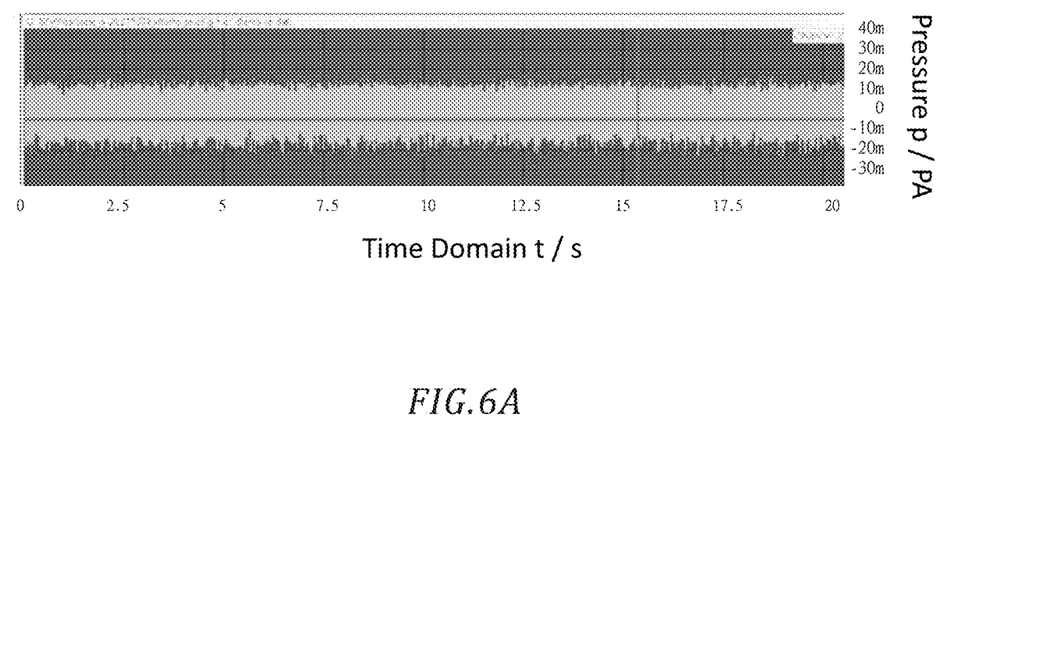
FIG. 6A shows the test results of the test item 1 performed in the Bell Mode specification on a conventional planar diaphragm.
Figure 6B:
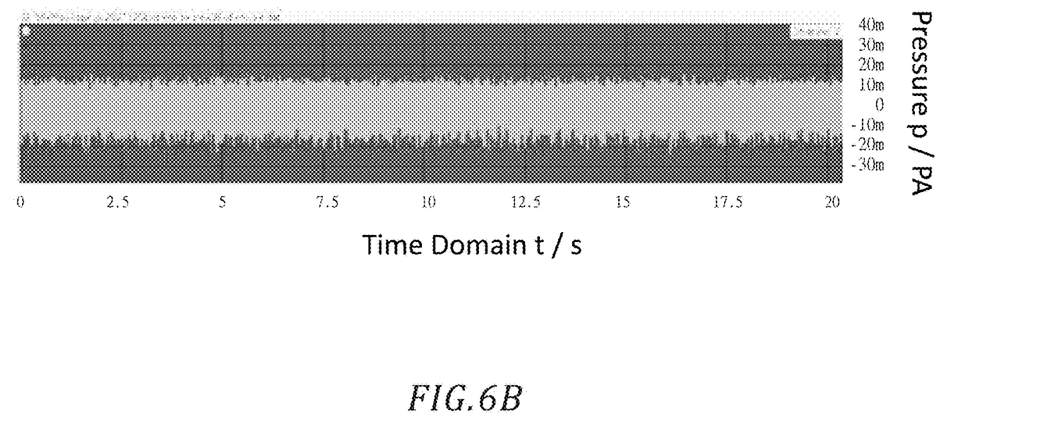
FIG. 6B shows the test results of the test item 1 performed in the Bell Mode specification on the pickup diaphragm according to the present invention.
Figure 7A:
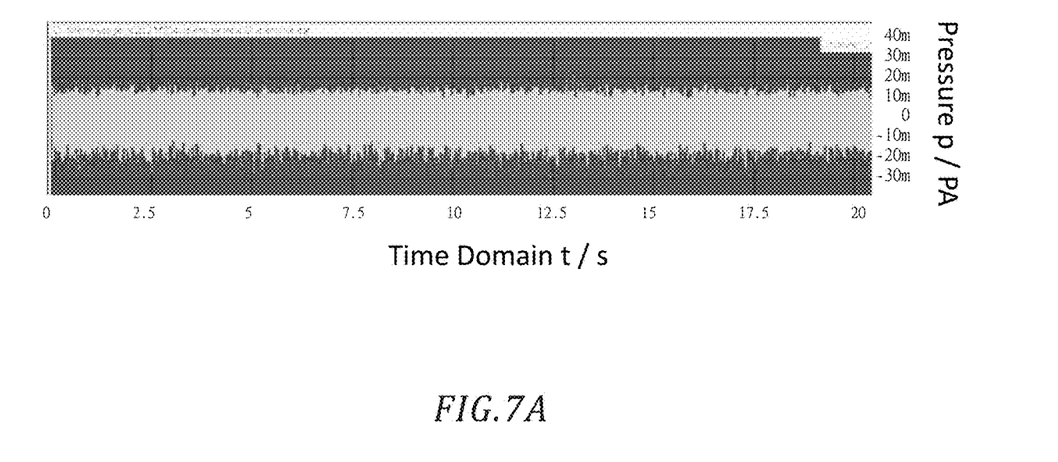
FIG. 7A shows the test results of the test item 1 performed in the Diaphragm Mode specification on the conventional planar diaphragm.
Figure 7B:
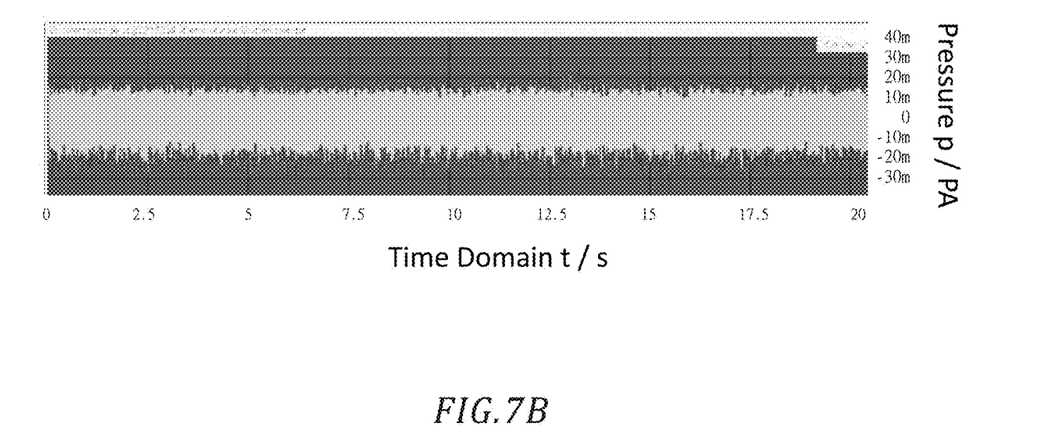
FIG. 7B shows the test results of the test item 1 performed in the Diaphragm Mode specification on the pickup diaphragm according to the present invention.
Figure 8A:
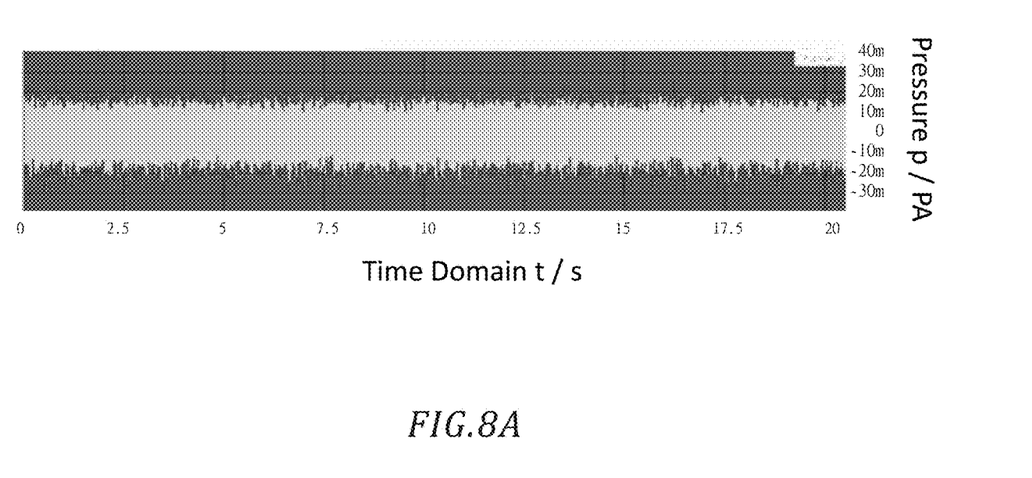
FIG. 8A shows the test results of the test item 1 performed in the Extended Range Mode specification on the conventional planar diaphragm.
Figure 8B:
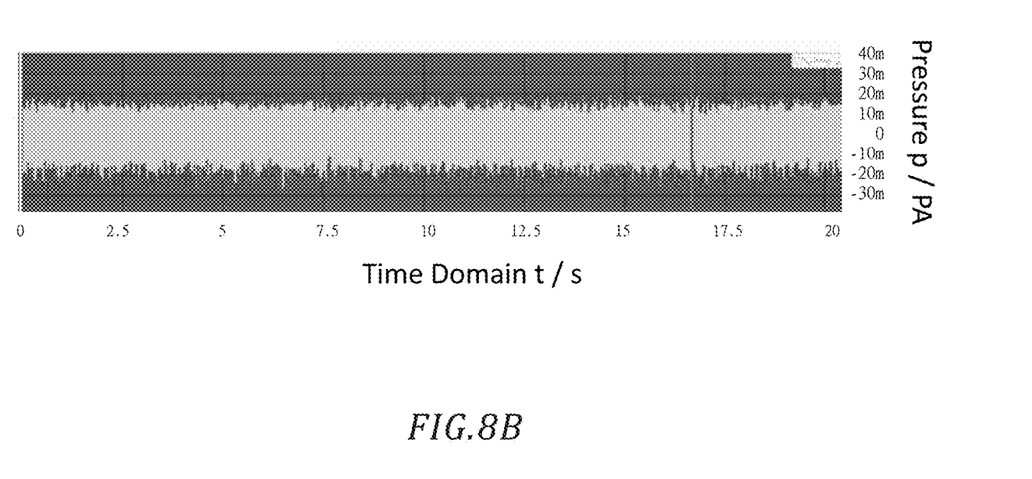
FIG. 8B shows the test results of the test item 1 performed in the Extended Range Mode specification on the pickup diaphragm according to the present invention.

The results of each of such comparisons in TEST ITEM 1 are shown in the Figures, wherein FIGS. 6A and 6B are comparison tests of Bell mode specifications, FIGS. 7A and 7B comparison tests of Diaphragm mode specifications, and FIGS. 8A and 8B comparison tests of Extended Range mode specifications. After comparison in this test, it can be seen that the frequency responses of the two test objects under idle noise are not significantly different.

Test Item 2—Comparative Tests of the Present Invention and Conventional Products Under White Noise Identically, the test hardware is configured in an anechoic chamber, and the test objects are stethoscopes/heads using the pickup diaphragm according to the present invention and stethoscopes/heads using conventional planar diaphragm products. Additionally, the stethoscope/head of the pickup diaphragm according to the present invention is tested in three specifications: Bell mode, Diaphragm mode, and Extended Range mode, which is sequentially and respectively placed on the speaker inside the test environment in a diaphragm surface facing-down fashion, and applies clay and weights to attach onto the stethoscope thus ensuring that the entire diaphragm surface can be tightly attached to the speaker. Then, while the ACQUAlyzer plays the white noise through the speaker (the volume is adjusted to level 1), it is possible to observe the sound reception condition of the test object under the receivable maximum sound reception level (gain: 0 dB).

Figure 9A:
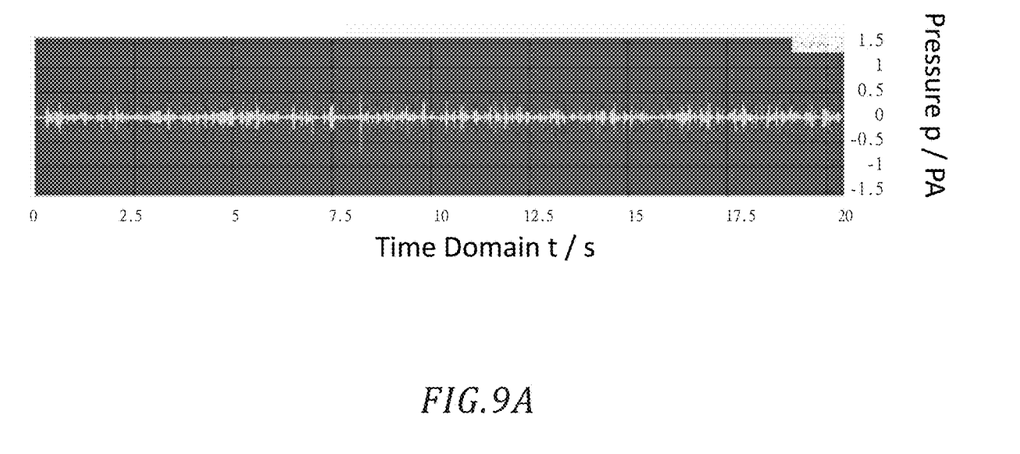
FIG. 9A shows the test results of the test item 2 performed in the Bell Mode specification on the conventional planar diaphragm.
Figure 9B:
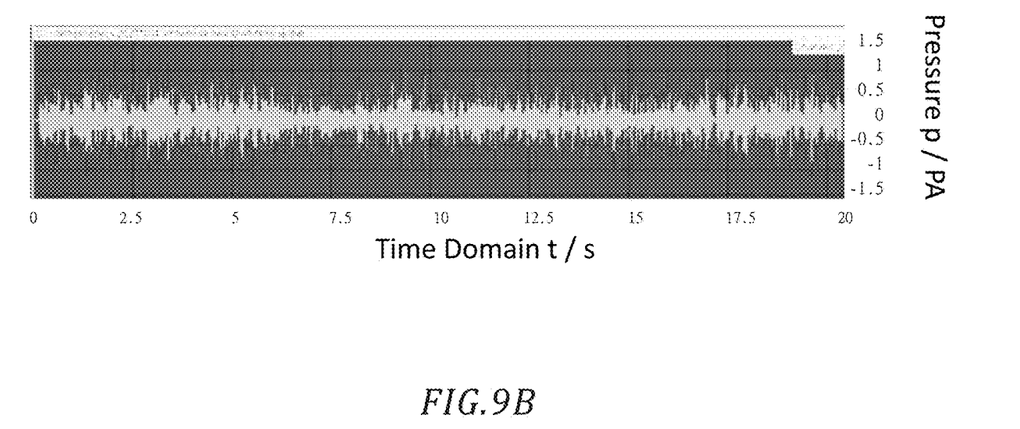
FIG. 9B shows the test results of the test item 2 performed in the Bell Mode specification on the pickup diaphragm according to the present invention.
Figure 10A:
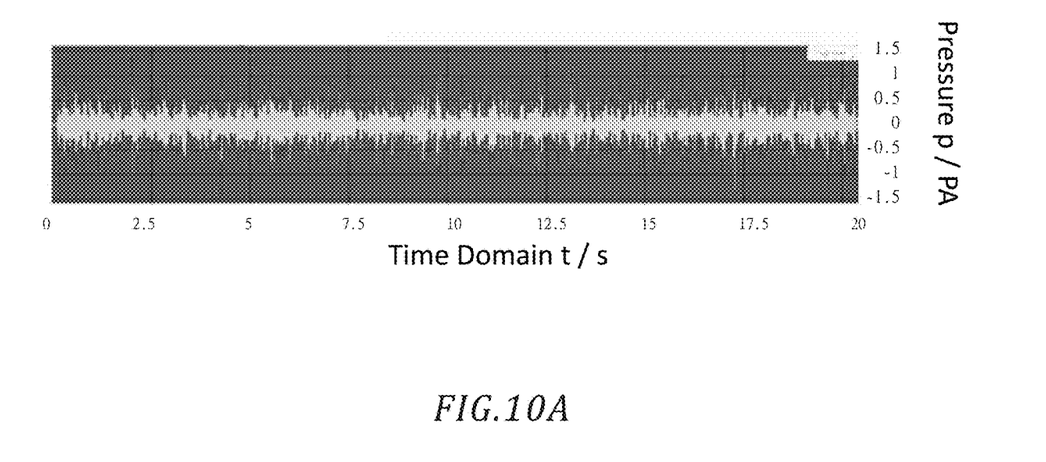
FIG. 10A shows the test results of the test item 2 performed in the Diaphragm Mode specification on the conventional planar diaphragm.
Figure 10B:
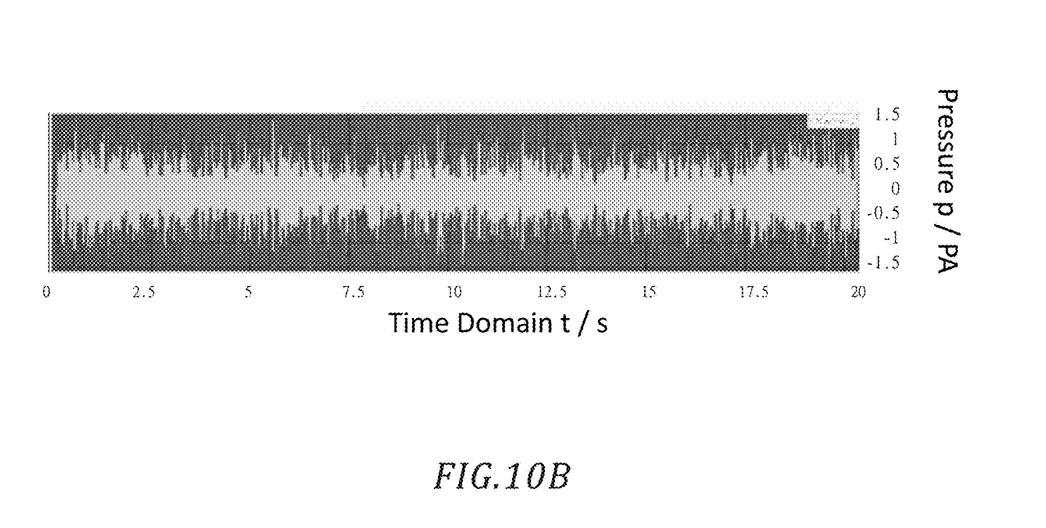
FIG. 10B shows the test results of the test item 2 performed in the Diaphragm Mode specification on the pickup diaphragm according to the present invention.
Figure 11A:
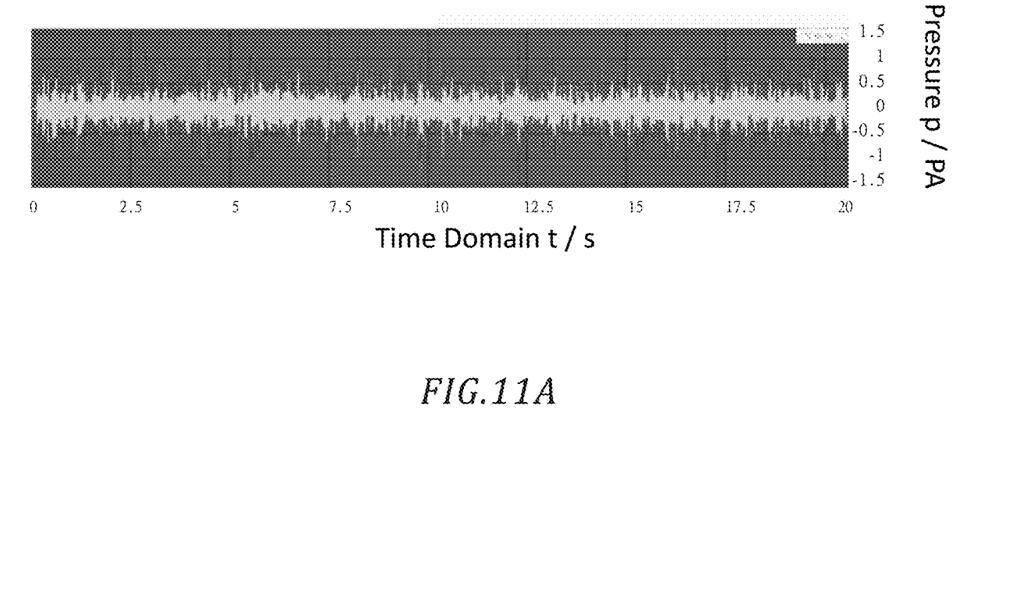
FIG. 11A shows the test results of the test item 2 performed in the Extended Range Mode specification on the conventional planar diaphragm.
Figure 11B:
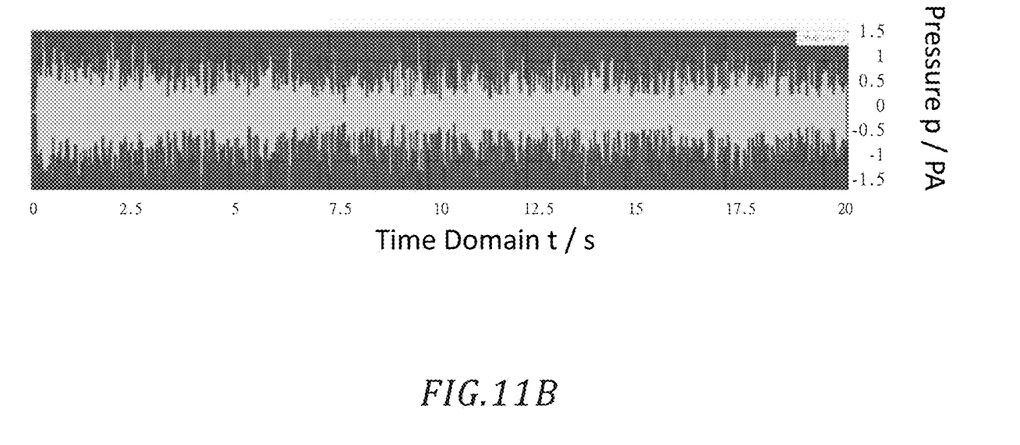
FIG. 11B shows the test results of the test item 2 performed in the Extended Range Mode specification on the pickup diaphragm according to the present invention.

The results of each of such comparisons in TEST ITEM 2 are shown in the Figures, wherein FIGS. 9A and 9B are comparison tests of Bell mode specifications, FIGS. 10A and 10B comparison tests of Diaphragm mode specifications, and FIGS. 11A and 11B comparison tests of Extended Range mode specifications. After comparison in this test, regarding to the two test objects under white noise, it can be seen that the frequency responses acquired by the stethoscope/head using the pickup diaphragm according to the present invention are significantly higher than those of the conventional products.

Through the aforementioned TEST ITEMS 1 to 2, it can be practically appreciated that the pickup diaphragm according to the present invention indeed provides better application results in practice.

It should be noticed that, although the present invention has been disclosed through the detailed descriptions of the aforementioned embodiments, such illustrations merely set forth partial selections for the preferred embodiments of the present invention and are by no means used to restrict the scope thereof; that is, those skilled ones in relevant fields of the present invention can certainly devise any applicable alternations and modifications after having comprehended the aforementioned technical characteristics and embodiments of the present invention without departing from the spirit and scope thereof. Hence, the scope of the present invention to be protected under patent laws should be delineated in accordance with the claims set forth hereunder in the present specification.

What is claimed is:

1. A pickup diaphragm, detachably installed in sleeve on a stethoscope head, comprising:
   a pickup part, used for picking up an audio and including a non-planar surface which is concave toward the stethoscope head, wherein the non-planar surface is a tapered surface;
   a suspension edge, including a deformable surface, in which a joint surface is respectively configured on the inner and outer sides of the deformable surface, and the joint surface on the inner side is fixedly connected to the periphery of the non-planar surface wherein the pickup part and the suspension edge are configured to have different materials and shapes so that the non-planar surface deforms during an audio pickup process; and
   an outer edge, including a ring groove, in which one side of the ring groove is set as a connection end while the other side thereof is set as an opening end, the inner side of the connection end is fixedly connected to the joint surface located on the outer side, and the stethoscope head is inserted through the opening end, such that the ring groove is placed in sleeve on the outside of the stethoscope head.

2. The pickup diaphragm according to claim 1, wherein the pickup part is manufactured by means of bio-compatible PP (Polypropylene) materials.

3. The pickup diaphragm according to claim 1, wherein the suspension edge is manufactured by means of fabrics processed with bio-compatible coating surface treatment.

4. The pickup diaphragm according to claim 1, wherein the outer edge is manufactured by means of elastic PP materials.

5. The pickup diaphragm according to claim 1, wherein the deformable surface is an arc-shaped or arbitrary curved surface.

* * * * *